United States Patent
Bauer et al.

(10) Patent No.: US 8,221,658 B2
(45) Date of Patent: Jul. 17, 2012

(54) MIXED SALTS OF DIORGANYLPHOSPHINIC ACIDS AND CARBOXYLIC ACIDS

(75) Inventors: Harald Bauer, Kerpen (DE); Werner Krause, Huerth (DE); Wolfgang Wanzke, Augsburg (DE)

(73) Assignee: Clariant Finance (BVI) Limited, Tortola (VG)

( * ) Notice: Subject to any disclaimer, the term of this patent is extended or adjusted under 35 U.S.C. 154(b) by 275 days.

(21) Appl. No.: 12/313,523

(22) Filed: Nov. 21, 2008

(65) Prior Publication Data

US 2009/0137707 A1 May 28, 2009

(30) Foreign Application Priority Data

Nov. 26, 2007 (DE) .......................... 10 2007 057 210

(51) Int. Cl.
*C09K 21/00* (2006.01)
*C09K 21/04* (2006.01)
*C07F 9/28* (2006.01)

(52) U.S. Cl. ............................ 252/609; 252/601; 562/8
(58) Field of Classification Search .................. 252/601, 252/609; 562/8
See application file for complete search history.

(56) References Cited

U.S. PATENT DOCUMENTS

| | | | |
|---|---|---|---|
| 3,001,938 A * | 9/1961 | Morway et al. ................ | 508/429 |
| 4,038,249 A * | 7/1977 | Spivack et al. ................. | 524/91 |
| 6,365,071 B1 | 4/2002 | Jenewein | |

FOREIGN PATENT DOCUMENTS

WO WO 97/39053 10/1997

OTHER PUBLICATIONS

EPO Search Report for EP 08020200, mailed Mar. 17, 2011.

* cited by examiner

*Primary Examiner* — Peter F Godenschwager
(74) *Attorney, Agent, or Firm* — Anthony A. Bisulca

(57) ABSTRACT

The invention relates to mixtures of diorganylphosphinic acids and carboxylic acids of the formula

[cation$^{n+}$(phosphinate$^-$)$_x$(carboxylic acid anion$^{z-}_{1/z}$)$_y$]

where
n=from 1 to 4
x=from 0.01 to n−0.01
y=n−x
z=from 1 to 4,
where
"cation" means an element of the second main and/or transition group, an element of the third main and/or transition group, an element of the fourth main and/or transition group, an element of the fifth main and/or transition group, an element of the sixth transition group, an element of the seventh transition group, and/or an element of the eighth transition group,
"phosphinate" means the anion of diorganylphosphinic acids of the formula

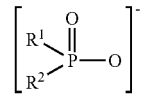

where
$R^1$ and $R^2$ are identical or different and, independently of one another, are H, $C_1$-$C_6$-alkyl, linear or branched, and/or aryl, and/or hydroxyalkyl, and
"carboxylic acid anion" means $C_1$-$C_{18}$ carboxylic acid anions.
The invention also relates to processes for their production, and to their use.

12 Claims, No Drawings

MIXED SALTS OF DIORGANYLPHOSPHINIC ACIDS AND CARBOXYLIC ACIDS

The present invention is described in the German priority application No. 102007057210.9, filed 26 Nov. 2007, which is hereby incorporated by reference as is fully disclosed herein.

The invention relates to mixed salts of diorganylphosphinic acids and carboxylic acids, to a process for their preparation, and to their use.

The prior art describes a number of phosphinic salts, some of which have considerable thermal stability. By way of example, under nitrogen the aluminum salt of diisobutylphosphinic acid evaporates at from 300 to 400° C., and the aluminum salt of diethylphosphinic acid evaporates to some extent at from 400 to 500° C. However, experience has shown that the stability of said salts in air is lower, because of onset of oxidation reactions.

However, flame retardants for high-performance plastics have to be processable at a particularly high temperature. It was therefore the object of the invention to provide flame retardants of particular thermal stability.

Surprisingly, it has been found that mixed salts of diorganylphosphinic acids and carboxylic acids achieve said object.

Surprisingly, the mixed salts of the invention moreover achieve a further important precondition for high flame retardant effectiveness: high content of aromatic fractions in the molecule can promote the formation of flame-retardant insulation layers (char). Provision of this novel class of compound can provide examples with particularly high aromatic content.

The invention therefore provides mixed salts of diorganylphosphinic acids and carboxylic acids of the formula (I)

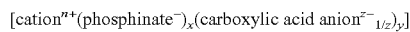

where
n=from 1 to 4
x=from 0.01 to n−0.01
y=n−x
z=from 1 to 4,
where
"cation" means an element of the second main and/or transition group, an element of the third main and/or transition group, an element of the fourth main and/or transition group, an element of the fifth main and/or transition group, an element of the sixth transition group, an element of the seventh transition group, and/or an element of the eighth transition group,
"phosphinate" means the anion of diorganylphosphinic acids of the formula (II)

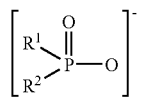

where
$R^1$ and $R^2$ are identical or different and, independently of one another, are H, $C_1$-$C_6$-alkyl, linear or branched, and/or aryl, and/or hydroxyalkyl, and
"carboxylic acid anion" means $C_1$-$C_{18}$ carboxylic acid anions.

The cation is preferably at least one from the group of Mg, Ca, Al, Sb, Sn, Ge, Ti, Fe, Zr, Zn, Ce, Bi, Sr, and/or Mn.

It is preferable that $R^1$ and $R^2$ are identical or different and, independently of one another, are H, methyl, ethyl, n-propyl, isopropyl, n-butyl, sec-butyl, tert-butyl, n-pentyl and/or phenyl, hydroxymethyl, hydroxyethyl, and/or hydroxypropyl.

It is preferable that the carboxylic acids are polybasic and/or aromatic $C_8$-$C_{18}$ carboxylic acids and/or $C_8$-$C_{18}$ omega-aminocarboxylic acids.

It is preferable that the carboxylic acid is terephthalic acid, phthalic acid, isophthalic acid, and/or ethylene glycol-terephthalic acid oligomer.

It is preferable that the mixed salts of diorganylphosphinic acids and carboxylic acids are aluminum isophthalate diethylphosphinate, aluminum terephthalate diethylphosphinate, or dizinc monoterephthalate mono(diethylphosphinate).

The present object is also achieved via a process (1) for the preparation of mixed salts of diorganylphosphinic acids and carboxylic acids, which comprises reacting
a) a phosphinic acid source with
b) a cation source.

In the process (1) it is preferable that the molar ratio of phosphinic acid source to cation source is from 100:1 to 1:10.

The cation source for the process (1) is preferably aluminum terephthalate, aluminum phthalate, aluminum isophthalate, zinc terephthalate, zinc phthalate, and/or zinc isophthalate; the aluminum, zinc, titanium, and/or iron salts of $C_1$-$C_{18}$ carboxylic acids; or metal soaps.

A further process (2) for the preparation of mixed salts of dialkylphosphinic acids and dicarboxylic acids comprises reacting
a) a carboxylic acid with
b) a cation source.

It is preferable that in the process (2) the molar ratio of carboxylic acid to cation source is from 100:1 to 1:10.

It is preferable that the cation source for the process (2) is aluminum hypophosphite, calcium hypophosphite, magnesium hypophosphite, aluminum tris(monoethylphosphinate), aluminum tris(diethylphosphinate), iron tris(diethylphosphinate), calcium bis(diethylphosphinate), magnesium bis(diethylphosphinate), zinc bis(diethylphosphinate), titanium tetrakis(diethylphosphinate), titanyl diethylphosphinate $TiO_x(PO_2(C_2H_5)_2)_{4-2x}$, aluminum tris(methylethylphosphinate), aluminum tris(butylethylphosphinate), aluminum tris(dibutylphosphinate) and/or aluminum tris(bishydroxymethylphosphinate).

The invention also provides a process (3) for the preparation of mixed salts of dialkylphosphinic acids and dicarboxylic acids, which comprises reacting
a) a carboxylic acid or one of its salts with
b) a phosphinic acid source, and
c) a cation source.

It is preferable that in the process (3) the molar ratio of phosphinate source to cation source is from 100:1 to 1:10, and the molar ratio of carboxylic acid to cation source is from 100:1 to 1:10.

It is preferable that the cation source for the process (3) is zinc compounds, aluminum hydroxide, boehmite, gibbsite, hydrotalcite, and/or titanium dioxide.

It is preferable that the carboxylic acid is terephthalic acid, phthalic acid, isophthalic acid, ethylene glycol-terephthalic acid oligomer, or one of their salts.

It is preferable that the phosphinic acid source is hypophosphorous acid, methylphosphonous acid, ethylphosphonous acid, diethylphosphinic acid, ethylmethylphosphinic acid, butylethylphosphinic acid, dibutylphosphinic acid, and/or bis(hydroxymethyl)phosphinic acid.

The invention also provides the use of mixed salts of diorganylphosphinic acids and carboxylic acids as claimed in one or more of claims 1 to 6 in flame retardants or flame retardant mixtures.

Accordingly, the invention then also provides a flame retardant, comprising
a) from 0.1% to 99.9% by weight of mixed salts of diorganylphosphinic acids and carboxylic acids, as claimed in one or more of claims 1 to 6 and
b) from 0.1% to 99.9% by weight of cation source.

Accordingly, the invention then also provides a flame retardant, comprising
a) from 7% to 90% by weight of mixed salts of diorganylphosphinic acids and carboxylic acids, as claimed in one or more of claims 1 to 6
b) from 10% to 93% by weight of cation source.

Accordingly, the invention then also provides a flame retardant, comprising
a) from 65 to 90% by weight of mixed salts of diorganylphosphinic acids and carboxylic acids, as claimed in one or more of claims 1 to 6, and
b) from 10 to 35% by weight of cation source.

The invention also provides a flame retardant mixture, comprising
a) from 0.1 to 99.9% by weight of mixed salts of diorganylphosphinic acids and carboxylic acids, as claimed in one or more of claims 1 to 6 and
b) from 0.1 to 99.9% by weight of at least one member of the group of the cation sources and/or synergists.

The invention also provides a flame retardant mixture, comprising
a) from 25 to 75% by weight of mixed salts of diorganylphosphinic acids and carboxylic acids, as claimed in one or more of claims 1 to 6 and
b) from 75 to 25% by weight of at least one member of the group of the cation sources and/or synergists.

The invention also provides the use of mixed salts of diorganylphosphinic acids and carboxylic acids as claimed in one or more of claims 1 to 6 as flame retardant booster, as flame retardants for clearcoat lacquers and intumescent coatings, flame retardants for wood and other cellulose-containing products, or as reactive and/or non-reactive flame retardant for polymers, and/or for providing flame retardancy to polyester and to unblended or blended cellulose textiles, via impregnation.

The use of mixed salts of diorganylphosphinic acids and carboxylic acids, as claimed in one or more of claims 1 to 6, is likewise claimed as binders for foundry materials and molding sands; as crosslinking agents or accelerator in the hardening of epoxy resins, of polyurethanes, or of unsaturated polyester resins;

as polymer stabilizers, e.g. as light stabilizer, free-radical scavenger, and/or heat stabilizer for cotton fabrics, polymer fibers, plastics; as crop protection agent, e.g. as plant growth regulator, or as herbicide, pesticide, or fungicide;

as therapeutic agent or additive in therapeutic agents for humans and animals, e.g. as enzyme modulator, for stimulation of tissue growth;

as sequestering agent, e.g. for the control of deposits in industrial water supply systems, in petroleum production, and in metal-treatment agents;

as petroleum additive, e.g. as antioxidant, and for increasing octane number; or as corrosion-prevention agent;

in laundry-detergent and cleaning-product applications, e.g. as decolorizer;

in electronics applications, e.g. in polyelectrolytes for capacitors, batteries, and accumulators, or else as free-radical scavengers in photosensitive layers;

as aldehyde scavengers;

or as formaldehyde scavengers in adhesive compositions and in moldings, e.g. in construction applications, in the automobile industry, in shipbuilding, in the aerospace industry, and for electrical engineering.

The invention also provides a flame-retardant polymer molding composition, comprising
from 0.1 to 39% by weight of mixed salts of diorganylphosphinic acids and carboxylic acids, as claimed in one or more of claims 1 to 6,
from 0.5 to 98.9% by weight of polymer or of a mixture of the same,
from 0.5 to 50% by weight of additives, and
from 0 to 50% by weight of filler or reinforcing materials,
where the entirety of the components is 100% by weight.

The invention also provides flame-retardant polymer molding compositions, comprising
from 0.5 to 45% by weight of flame retardant and/or flame retardant mixtures which comprise mixed salts of diorganylphosphinic acids and carboxylic acids, as claimed in one or more of claims 1 to 6,
from 0.5 to 98.5% by weight of polymer or of a mixture of the same,
from 0.5 to 50% by weight of additives, and
from 0 to 50% by weight of filler or reinforcing materials,
where the entirety of the components is 100% by weight.

Finally, the invention also provides flame-retardant polymer moldings, flame-retardant films, flame-retardant polymer filaments, and flame-retardant polymer fibers, comprising from 1 to 50% by weight of mixed salts of diorganylphosphinic acids and carboxylic acids, flame retardants and/or flame retardant mixtures which comprise mixed salts of diorganylphosphinic acids and carboxylic acids, as claimed in one or more of claims 1 to 6,
from 1 to 99% by weight of polymer or a mixture of the same,
from 0 to 60% by weight of additives, and
from 0 to 60% by weight of filler,
where the entirety of the components is 100% by weight.

The novel mixed salts of diorganylphosphinic acids and carboxylic acids of the formula (I) of the invention are not simple physical mixtures of metal phosphinates and metal carboxylates, but are novel chemical compounds.

The crystal lattice of the novel compounds characteristically differs from that of the comparable phosphinates and carboxylates. This can be demonstrated by generating an X-ray powder diffractogram and qualitative evaluation of the reflections.

The novel mixed salts of diorganylphosphinic acids and carboxylic acids of the formula (I) of the invention also differ markedly from the compounded materials and, respectively, coextrudates known hitherto, in which there are metal phosphinates uniformly physically dispersed in oligomers or polymers of mono- or polybasic carboxylic acids. Examples of these extrudates are flame-retardant polymeric molding compositions in which there are metal phosphinates embedded in particle form into the polymer, but where no chemical reaction has taken place between the components to form mixed salts.

The novel mixed salts of diorganylphosphinic acids and carboxylic acids of the formula (I) of the invention likewise differ markedly from the metal phosphinates known hitherto which are coated with oligomers, with polymers, or with esters of mono- or polybasic carboxylic acids. This type of coating can be carried out by dispersing a metal phosphinate and di-2-ethylhexyl phthalate in water, filtering, and drying.

This type of coating can also be carried out by another method, by mixing a metal phosphinate and di-2-ethylhexyl phthalate in a mixer and, if appropriate, heat-treating the mixture. In both cases, no chemical reaction takes place between the phthalic ester and the metal phospinate, and nor are the novel mixed salts of diorganylphosphinic acids and carboxylic acids of the formula (I) of the invention obtained.

Systems similar to the invention can possibly be produced to a very small extent when a metal phosphinate reacts with mono- or polybasic carboxylic acids produced by decomposition of the polymer, to give mixed salts which cannot be defined in any great detail. This preferably occurs during thermal stressing of metal phosphinate-polymer mixtures, or of extrudates or moldings. The thermal stressing can arise during compounding, extrusion, injection molding, or during storage under hot conditions or in the event of a fire, or via contact with smoldering articles. However, controlled preparation of mixtures as claimed in claims 1 to 6, in the claimed quantitative proportions, was neither possible hitherto nor known.

In a further embodiment, the carboxylic acids are formed from precursors. They can be formed via thermal decomposition or reaction of the precursors with water. Preferred precursors are nitriles of the underlying carboxylic acids, e.g. terephthalonitrile, phthalonitrile, adiponitrile, and also the amides and the esters of the carboxylic acids. The molar ratio of precursor to water is preferably from 100:1 to 1:100. The temperature during formation from the precursor is from 20 to 500° C., preferably from 150 to 350° C.

The mono- or polybasic carboxylic acids can preferably also be produced by chain fragmentation, hydrolysis, thermolysis, rearrangement of polyesters (polybutylene terephthalate, polytrimethylene terephthalate, polyethylene terephthalate) and of polyamides (PA6, PA6.6, high-temperature nylon).

Preferred carboxylic acids are formic acid, acetic acid, propionic acid, butyric acid, valeric acid (pentanoic acid), caproic acid (hexanoic acid), enanthic acid (heptanoic acid, heptylic acid), caprylic acid (octanoic acid), pelargonic acid (n-nonanoic acid), capric acid (decanoic acid), h-hendecanoic acid (undecanoic acid), 8-methylcapric acid, lauric acid (dodecanoic acid), myristic acid (tetradecanoic acid), palmitic acid (cetylic acid, hexadecanoic acid), stearic acid (octadecanoic acid), oleic acid (cis-9-octadecenoic acid), elaidic acid (trans-9-octadecenoic acid), nonadecanoic acid, arachic acid (arachidinic acid, icosanic acid, eicosanic acid), behenic acid (docosanoic acid), montanic acid, and/or sulfobenzoic acid hydrate.

Preferred omega-aminocarboxylic acids (i.e. having chain-terminal amino groups, or their lactams and cyclic anhydrides) are alpha-amino acids, beta-amino acids (beta-aminopropionic acid), gamma-aminocarboxylic acids, (gamma-aminobutyric acid, gamma-butyrolactam), epsilon-aminocaproic acid (epsilon-caprolactam), 11-aminoundecanoic acid, and/or laurolactam.

Polybasic carboxylic acids are preferred.

Preference is given here to oxalic acid, malonic acid (propanedioic acid), methylmalonic acid, succinic acid, methylsuccinic acid, cyclopropane-1,1-dicarboxylic acid, adipic acid (hexanedioic acid), pimelic acid (heptanedioic acid), suberic acid, (octanedioic acid), azelaic acid (nonanedioic acid, heptane-1,7-dicarboxylic acid), sebacic acid (decanedioic acid), 1,12-dodecanedioic acid, brassylic acid, 1,14-tetradecanedioic acid, citric acid, isocitric acid, and/or nitrilotriacetic acid.

Preference is given to polybasic, aromatic $C_{8-18}$ carboxylic acids.

Particular preference is given here to terephthalic acid, phthalic acid, isophthalic acid and/or ethylene glycol-terephthalic acid oligomer, with a molar mass of from 228 to 18 000 g/mol.

Preference is given to carboxylic acids whose boiling point is from 100 to 500° C. at atmospheric pressure, particularly preferably from 200 to 420° C.

It is preferable that the quotient of boiling point of the carboxylic acid with respect to the boiling point of the phosphinic acid is from 0.62 to 1.18, particularly preferable from 0.76 to 1.18.

Preference is given to carboxylic acids whose pKa1 value is in the range from 1.25 to 4.0 and whose pKa2 value is from 3.81 to 5.5.

Preference is given to carboxylic acids whose acid number is in the range from 340 to 730 mg KOH/g.

Preference is given to carboxylic acids whose carbon content is from 54 to 64% by weight.

The formation of flame-retardant insulation layers (char) is an important fundamental effect for flame retardancy. By virtue of their high thermal stability, mixed salts of the invention can form char, or char can be composed of the same. For improvement of the flame-retardant effect of flame retardants, of flame retardant mixtures, of flame-retardant molding compositions, and of flame-retardant moldings, the mixed salts of the invention can be added to these, or mixed salts of the invention can be formed by chemical reaction from polymer and diorganylphosphinic salt (aluminum trisdiethylphosphinate, etc.).

It is preferable that the residual moisture level of the mixed salts of the invention of diorganylphosphinic acids and carboxylic acids is from 0.01 to 10% by weight, particularly preferably from 0.1 to 1% by weight. Values outside of the abovementioned ranges imply high production cost or relatively poor compatibility with polymers.

It is preferable that the particle size of the mixed salts of diorganylphosphinic acids and carboxylic acids of the invention is from 0.1 to 1000 μm, particularly from 10 to 100 μm. Values outside of the abovementioned ranges imply high production cost or relatively poor compatibility with polymers.

It is preferable that the bulk density of the mixed salts of diorganylphosphinic acids and carboxylic acids of the invention is from 80 to 800 g/l, particularly preferably from 200 to 700 g/l.

It is preferable that the solubility of the mixed salts of diorganylphosphinic acids and carboxylic acids of the invention in water and/or organic solvents, such as alcohols, glycols, aliphatic hydrocarbons, alicyclic hydrocarbons, aromatic hydrocarbons, halogenated hydrocarbons, ethers, glycol ethers, ketones, esters, and/or carboxylic acids is from 0.001 to 10% by weight. Higher values incur a risk of blooming.

The mixed salts of diorganylphosphinic acids and carboxylic acids of the invention have preferred L color coordinates of from 85 to 99.9, particularly from 90 to 98. Diorganylphosphinic salts whose L coordinates are below the range of the invention require relatively high use of white pigment. This impairs the mechanical stability properties of the polymer molding (e.g. modulus of elasticity). Lower values often require the use of compensating white pigments.

The mixed salts of diorganylphosphinic acids and carboxylic acids of the invention have preferred a color coordinates from −4 to +9, particularly from −2 to +6.

The mixed salts of diorganylphosphinic acids and carboxylic acids of the invention have preferred b color coordinates from −2 to +6, particularly from −1 to +3.

The color coordinates are stated in the Hunter system (CIE-LAB-System, Commission Internationale d'Eclairage). L coordinates range from 0 (black) to 100 (white), a coordinates from −a (green) to +a (red), and b coordinates from −b (blue) to +b (yellow).

Mixed salts of diorganylphosphinic acids and carboxylic acids whose a and, respectively, b coordinates are outside of the range of the invention require relatively high use of white pigment. This impairs the mechanical stability properties of the polymer molding (e.g. modulus of elasticity).

The preferred weight loss of the mixed salts of diorganylphosphinic acids and carboxylic acids of the invention in differential thermal analysis in air is 2% at temperatures of from 350 to 500° C.

Surprisingly, the thermal stability of the mixed salts of diorganylphosphinic acids and carboxylic acids of the invention is higher than that of the corresponding salts of the phosphinic acids and, respectively, salts of the carboxylic acids themselves.

The technical advance is obtained inter alia in that it is thus possible to prepare flame retardants which, when compared with the known flame retardants, permit a higher processing temperature. Particularly high-performance flame-retardant polymeric molding compositions and flame-retardant polymer moldings, flame-retardant polymer films, flame-retardant polymer filaments, and flame-retardant polymer fibers are often produced at relatively high processing temperatures. Using the novel flame retardants, they can for the first time be provided with flame retardancy, or even better flame retardancy properties can be achieved.

A preferred cation source in the process (3) is provided by zinc compounds, e.g. zinc oxide (e.g. activated zinc oxide from Rhein Chemie, Brüggermann K G, zincite or calamine; standard zinc oxide, G6 zinc white, 2011 zinc oxide, F-80 zinc oxide, Pharma 8 zinc white, Pharma A zinc white, or Rotsiegel zinc white, or Weissiegel zinc white from Grillo-Werke AG), zinc hydroxide, zinc oxide hydrate, anhydrous zinc carbonate, basic zinc carbonate, zinc hydroxide carbonate, basic zinc carbonate hydrate, zinc magnesium aluminum hydroxide carbonate), aluminum hydroxide, boehmite, gibbsite, hydrotalcite, or titanium dioxide.

The reaction of the process (3) preferably takes place in a solvent. Solvents suitable in the invention are polar solvents, e.g. water, acetic acid, and/or the actual polybasic carboxylic acid used.

The reaction of processes 1 to 3 of the invention preferably takes place at a temperature of from −20 to +600° C., particularly preferably from 200 to 500° C.

It is preferable that the reaction time in processes 1 to 3 is from 0.01 to 100 h, particularly from 1 to 10 h.

It is preferable that the pressure for the formation process in the processes 1 to 3 is from 10 to 100 000 000 Pa.

It is preferable that the atmosphere for the processes 1 to 3 comprises from 0.001 to 10% by volume of oxygen, and from 90 to 99.999% by volume of inert gases. It is preferable that inert gases are nitrogen, argon, or carbon dioxide.

It is preferable that apparatuses are mixers, kneaders, rotating-tube furnaces, tray ovens, belt ovens, fluidized beds, stirred autoclaves, stirred tanks, ball mills.

In another embodiment, the flame retardant can be produced by a substoichiometric reaction of polybasic carboxylic acid and cation source.

It is preferable that the flame retardant mixtures of the invention also comprise at least one synergist.

It is preferable that the flame retardant mixtures of the invention then comprise a) from 0.1% to 99.8% by weight of mixed salts of diorganylphosphinic acids and carboxylic acids of the invention, and b) from 0.1% to 99.8% by weight of synergist.

It is preferable that the flame retardant mixtures of the invention also comprise a) from 0.1% to 99.7% by weight of mixed salts of diorganylphosphinic acids and carboxylic acids of the invention b) from 0.1% to 99.7% by weight of cation source, and c) from 0.1% to 99.7% by weight of synergist.

Suitable synergists are melamine phosphate, dimelamine phosphate, melamine pyrophosphate, melamine polyphosphates, melam polyphosphates, melem polyphosphates, and/or melon polyphosphates; melamine condensates, such as melam, melem, and/or melon; condensates of melamine (melem, melam, or melon, or compounds of this type having a higher degree of condensation, and also mixtures of the same), or reaction products of melamine with phosphoric acid, or reaction products of condensates of melamine with phosphoric acid, and also mixtures of the products mentioned.

The reaction products with phosphoric acid are compounds produced by reaction of melamine or of the condensed melamine compounds, such as melam, melem, or melon, etc., with phosphoric acid (melamine polyphosphate, melam polyphosphate, and melem polyphosphate, or mixed polysalts, etc.)

Other suitable synergists are oligomeric esters of tris(hydroxyethyl)isocyanurate with aromatic polycarboxylic acids, benzoguanamine, tris(hydroxyethyl)isocyanurate, allantoin, glycoluril, melamine, melamine cyanurate, dicyandiamide, and/or guanidine; nitrogen-containing phosphates of the formulae $(NH_4)_y H_{3-y} PO_4$ or $(NH_4 PO_3)_z$, where y is from 1 to 3 and z is from 1 to 10 000; nitrogen compounds of the formulae (III) to (VIII), or a mixture thereof

(III)

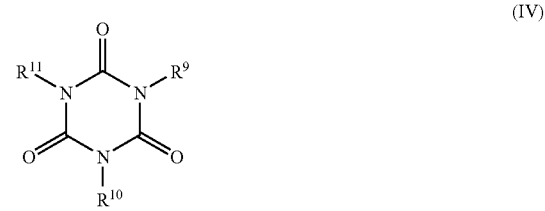

(IV)

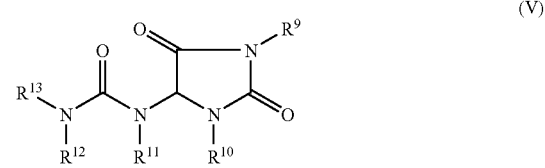

(V)

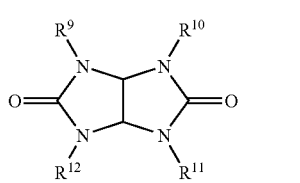

(VI)

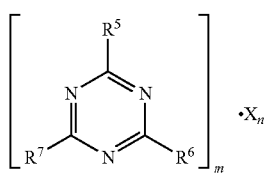

(VII)

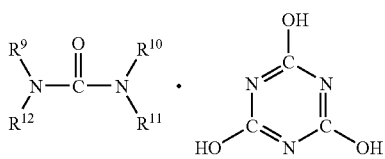

(VIII)

in which

R$^5$ to R$^7$ are hydrogen, C$_1$-C$_8$-alkyl, C$_5$-C$_{16}$-cycloalkyl or -alkylcycloalkyl, C$_2$-C$_8$-alkenyl, C$_1$-C$_8$-alkoxy, -acyl, -acyloxy, or C$_6$-C$_{12}$-aryl or -arylalkyl, —OR$^8$ and —N(R$^8$)R$^9$, including systems of N-alicyclic or N-aromatic type, R$^8$ is hydrogen, C$_1$-C$_8$-alkyl, C$_5$-C$_{16}$-cycloalkyl or -alkylcycloalkyl, C$_2$-C$_8$-alkenyl, C$_1$-C$_8$-alkoxy, -acyl, -acyloxy, or C$_6$-C$_{12}$-aryl or -arylalkyl, R$^9$ to R$^{13}$ are groups identical with R$^8$ or else —O—R$^8$, m and n, independently of one another, are 1, 2, 3, or 4, and X is acids which can form adducts with triazine compounds (III).

Other suitable synergists are oxygen compounds of silicon, magnesium compounds, metal carbonates of metals of the second main group of the Periodic Table of the Elements, red phosphorus, and zinc compounds and/or aluminum compounds. Among these are inter alia oxygen compounds of silicon such as salts and esters of orthosilicic acid and condensates thereof, silicates, zeolites, and silicas, glass powders, glass-ceramic powders, or ceramic powders; magnesium hydroxide, hydrotalcites, magnesium carbonates or magnesium calcium carbonates; zinc oxide, zinc stannate, zinc hydroxystannate, zinc phosphate, zinc borate, or zinc sulfides; aluminum hydroxide or aluminum phosphate.

The invention also provides the use of the mixed salts of diorganylphosphinic acids and carboxylic acids as flame retardant boosters, as flame retardants for clearcoat lacquers and intumescent coatings, flame retardants for wood and other cellulose-containing products, or as reactive and/or non-reactive flame retardant for polymers, and/or for providing flame retardancy to polyester and to unblended or blended cellulose textiles, via impregnation.

It is preferable that the polymer is a thermoplastic or thermoset polymer.

It is preferable that the polymers are polymers of mono- and diolefins, for example polypropylene, polyisobutylene, poly-1-butene, poly-4-methyl-1-pentene, polyisoprene, and polybutadiene, or else polymers of cycloolefins, e.g. of cyclopentene or norbornene; or polyethylene (which may, where appropriate, have been crosslinked), e.g. high-density polyethylene (HDPE), high-density high-molecular-weight polyethylene (HMWHDPE), high-density ultrahigh-molecular-weight polyethylene (UHMWHDPE), medium-density polyethylene (MDPE), low-density polyethylene (LDPE), linear low-density polyethylene (LLDPE), or branched low-density polyethylene (VLDPE), or a mixture thereof.

It is preferable that the polymers are copolymers of mono- and diolefins with one another or with other vinyl monomers, e.g. ethylene-propylene copolymers, linear low-density polyethylene (LLDPE), or a mixture of this with low-density polyethylene (LDPE), propylene-1-butene copolymers, propylene-isobutylene copolymers, ethylene-1-butene copolymers, ethylene-hexene copolymers, ethylene-methylpentene copolymers, ethylene-heptene copolymers, ethylene-octene copolymers, propylene-butadiene copolymers, isobutylene-isoprene copolymers, ethylene-alkyl acrylate copolymers, ethylene-alkyl methacrylate copolymers, ethylene-vinyl acetate copolymers and their copolymers with carbon monoxide, or ethylene-acrylic acid copolymers and their salts (ionomers), or else terpolymers of ethylene with propylene and with a diene, such as hexadiene, dicyclopentadiene, or ethylidenenorbornene; or a mixture of these copolymers with one another, e.g. polypropylene/ethylene-propylene copolymers, LDPE/ethylene-vinyl acetate copolymers, LDPE/ethylene-acrylic acid copolymers, LLDPE/ethylene-vinyl acetate copolymers, LLDPE/ethylene acrylic acid copolymers, and alternating or random-structure polyalkylene/carbon monoxide copolymers, or a mixture of these with other polymers, e.g. with polyamides.

It is preferable that the polymers are hydrocarbon resins (e.g. C$_5$-C$_9$) inclusive of hydrogenated modifications thereof (e.g. tackifier resins), and mixtures of polyalkylenes and starch.

It is preferable that the polymers are polystyrene (Polystyrol 143E from BASF), poly(p-methylstyrene), and/or poly (alpha-methylstyrene).

It is preferable that the polymers are copolymers of styrene or alpha-methylstyrene with dienes or with acrylic derivatives, e.g. styrene-butadiene, styrene-acrylonitrile, styrene-alkyl methacrylate, styrene-butadiene-alkyl acrylate and the corresponding methacrylate, styrene-maleic anhydride, styrene-acrylonitrile-methyl acrylate; a mixture of high impact resistance composed of styrene copolymers and of another polymer, e.g. of a polyacrylate, of a diene polymer, or of an ethylene-propylene-diene terpolymer; or else block copolymers of styrene, e.g. styrene-butadiene-styrene, styrene-isoprene-styrene, styrene-ethylene/butylene-styrene, or styrene-ethylene/propylene-styrene.

It is preferable that the polymers are graft copolymers of styrene or alpha-methylstyrene, e.g. styrene on polybutadiene, styrene on polybutadiene-styrene copolymers or on polybutadiene-acrylonitrile copolymers, styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene, styrene and alkyl acrylates and, respectively, alkyl methacrylates on polybutadiene, styrene and acrylonitrile on ethylene-propylene-diene terpolymers, styrene and acrylonitrile on polyalkyl acrylates or on polyalkyl methacrylates, styrene and acrylonitrile on acrylate-butadiene copolymers, or else a mixture of these, for example that known as ABS polymer, MBS polymer, ASA polymer, or AES polymer.

It is preferable that the polymers are halogen-containing polymers, e.g. polychloroprene, chlorinated rubber, chlorinated and brominated copolymer composed of isobutylene-isoprene (halobutyl rubber), chlorinated or chlorosulfonated polyethylene, copolymers of ethylene and of chlorinated ethylene, epichlorohydrinhomo- and copolymers, in particular polymers composed of halogen-containing vinyl compounds, e.g. polyvinyl chloride, polyvinylidene chloride, polyvinyl fluoride, polyvinylidene fluoride; or else copolymers of these, such as vinyl chloride-vinylidene chloride, vinyl chloride-vinyl acetate, or vinylidene chloride-vinyl acetate.

It is preferable that the polymers are polymers which derive from alpha-beta-unsaturated acids and from their derivatives, e.g. polyacrylates and polymethacrylates, butyl-acrylate-impact-modified polymethyl methacrylates, polyacrylamides and polyacrylonitriles, and copolymers of the monomers mentioned with one another or with other unsaturated monomers, e.g. acrylonitrile-butadiene copolymers, acrylonitrile-alkyl acrylate copolymers, acrylonitrile-alkoxyalkyl acrylate copolymers, acrylonitrile-vinyl halide copolymers, or acrylonitrile-alkyl methacrylate-butadiene terpolymers.

It is preferable that the polymers are polymers which derive from unsaturated alcohols and amines or from their acyl derivatives or acetals, e.g. polyvinyl alcohol, polyvinyl acetate, polyvinyl stearate, polyvinyl benzoate, polyvinyl maleate, polyvinyl butyral, polyallyl phthalate, polyallylmelamine; or else their copolymers with olefins.

It is preferable that the polymers are homo- and copolymers of cyclic ethers, e.g. polyalkylene glycols, polyethylene oxide, polypropylene oxide, or their copolymers with bisglycidyl ethers.

It is preferable that the polymers are polyacetals, such as polyoxymethylene, or else those polyoxymethylenes which contain comonomers, e.g. ethylene oxide; polyacetals modified with thermoplastic polyurethanes, or with acrylates, or with MBS.

It is preferable that the polymers are polyphenylene oxides and polyphenylene sulfides, and their mixtures with styrene polymers or with polyamides.

The polymers are preferably polyurethanes which derive firstly from polyethers, polyesters, and polybutadienes having terminal hydroxy groups, and secondly from aliphatic or aromatic polyisocyanates, or else are precursors of these.

It is preferable that the polymers are polyamides and copolyamides derived from diamines and dicarboxylic acids, and/or from aminocarboxylic acids, or from the corresponding lactams, for example nylon-2,12, nylon-4 (poly-4-aminobutyric acid, ®Nylon 4, DuPont), nylon-4,6 (poly(tetramethyleneadipamide), poly(tetramethyleneadipic diamide), ®Nylon 4/6, DuPont), nylon-6 (polycaprolactam, poly-6-aminohexanoic acid, ®Nylon 6, DuPont, ®Akulon K122, DSM; ®Zytel 7301, DuPont; ®Durethan B 29, Bayer), nylon-6,6 (poly(N,N'-hexamethyleneadipic diamide), ®Nylon 6/6, DuPont, ®Zytel 101, DuPont; ®Durethan A30, ®Durethan AKV, ®Durethan AM, Bayer; ®Ultramid A3, BASF), nylon-6,9 (poly(hexamethylenenonane diamide), ®Nylon 6/9, DuPont), nylon-6,10 (poly(hexamethylenesebacamide), ®Nylon 6/10, DuPont), nylon-6,12 (poly(hexamethylenedodecanediamide), ®Nylon 6/12, DuPont), nylon-6/6,6 (poly(hexamethyleneadipamide-co-caprolactam), ®Nylon 6/66, DuPont), nylon-7 (poly-7-aminoheptanoic acid, ®Nylon 7, DuPont), nylon-7,7 (polyheptamethylene-pimelamide, ®Nylon 7,7, DuPont), nylon-8 (poly-8-aminooctanoic acid, ®Nylon 8, DuPont), nylon-8,8 (polyoctamethylenesuberamide, ®Nylon 8,8, DuPont), nylon-9 (poly-9-aminononanoic acid, ®Nylon 9, DuPont), nylon-9,9 (polynonamethyleneazelamide, ®Nylon 9,9, DuPont), nylon-10 (poly-10-amino-decanoic acid, ®Nylon 10, DuPont), nylon-10,9 (poly(decamethyleneazelamide), ®Nylon 10,9, DuPont), nylon-10,10 (polydecamethylenesebacamide, ®Nylon 10,10, DuPont), nylon-11 (poly-11-aminoundecanoic acid, ®Nylon 11, DuPont), nylon-12 (polylaurolactam, ®Nylon 12, DuPont, ®Grillamid L20, Ems Chemie), aromatic polyamides derived from m-xylene, diamine, and adipic acid; polyamides prepared from hexamethylenediamine and iso- and/or terephthalic acid (polyhexamethyleneisophthalamide polyhexamethyleneterephthalamide) and, if appropriate, from an elastomer as modifier, e.g. poly-2,4,4-trimethylhexamethyleneterephthalamide or poly-m-phenyleneisophthalamide. Block copolymers of the abovementioned polyamides with polyolefins, with olefin copolymers, with ionomers, or with chemically bonded or grafted elastomers; or with polyethers, e.g. with polyethylene glycol, polypropylene glycol, or polytetramethylene glycol. Also EPDM- or ABS-modified polyamides or copolyamides; and also polyamides condensed during processing ("RIM polyamide systems").

It is preferable that the polymers are polyureas, polyimides, polyamideimides, polyetherimides, polyesterimides, polyhydantoins and polybenzimidazoles.

It is preferable that the polymers are polyesters which derive from dicarboxylic acids and dialcohols and/or from hydroxycarboxylic acids, or from the corresponding lactones, for example polyethylene terephthalate, polybutylene terephthalate (Celanex® 2500, Celanex® 2002, Celanese; Ultradur®, BASF), poly-1,4-dimethylolcyclohexane terephthalate, polyhydroxybenzoates, and also block polyetheresters which derive from polyethers having hydroxyl end groups; as well as polyesters modified with polycarbonates or with MBS.

Other suitable polymers are polycarbonates and polyester carbonates, polysulfones, polyether sulfones, and polyether ketones; crosslinked polymers which derive on the one hand from aldehydes and on the other hand from phenols, urea, or melamine, examples being phenol-formaldehyde resins, urea-formaldehyde resins, and melamine-formaldehyde resins; drying and non-drying alkyd resins.

It is preferable that the polymers are unsaturated polyester resins which derive from copolyesters of saturated and unsaturated dicarboxylic acids with polyhydric alcohols, and also vinyl compounds as crosslinking agents, or else the halogen-containing, low-flammability modified forms of these.

It is preferable that the polymers are crosslinkable acrylic resins which derive from substituted acrylic esters, e.g. from epoxy acrylates, from urethane acrylates, or from polyester acrylates.

It is preferable that the polymers are alkyd resins, polyester resins, and acrylate resins, crosslinked by melamine resins, by urea resins, by isocyanates, by isocyanurates, by polyisocyanates, or by epoxy resins.

It is preferable that the polymers are crosslinked epoxy resins which derive from aliphatic, cycloaliphatic, heterocyclic, or aromatic glycidyl compounds, e.g. products of bisphenol A diglycidyl ethers or of bisphenol F diglycidyl ethers, which are crosslinked by means of conventional hardeners, e.g. anhydrides or amines, with or without accelerators.

It is preferable that the polymers are mixtures (polyblends) of the abovementioned polymers, e.g. PP/EPDM, nylon/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PU, PC/thermoplastic PU, POM/acrylate, POM/MBS, PPO/HIPS, PPO/nylon-6,6 and copolymers, PA/HDPE, PA/PP, PA/PPO, PBT/PC/ABS, and PBT/PET/PC.

Preferred additives are flame retardant synergists, antioxidants, light stabilizers, antistatic agents, blowing agents, heat stabilizers, impact modifiers/processing aids, lubricants, release agents, antidripping agents, compatibilizers, nucleating agents, additives for laser marking, hydrolysis stabilizers, chain extenders, color pigments, and plasticizers.

Examples of preferred fillers and reinforcing agents are chalk and calcium carbonate, silicates, phyllosilicates, clay minerals, e.g. bentonites, montmorillonites, hectorites, saponites, precipitated/fumed/crystalline/amorphous silicas, glass fibers, glass beads, asbestos, talc, kaolin (China clay), mica, barium sulfate (baryte), carbon black, graphite, wood flour, and flours or fibers of other natural products, and synthetic fibers.

A process of the invention for the preparation of flame-retardant polymer molding compositions consists in mixing mixed salts of diorganylphosphinic acids and carboxylic acids and/or the flame retardant compositions with the polymer pellets and optionally additives in a mixer, and homogenizing the mixture in a suitable compounding assembly under conditions of the invention, in the polymer melt. The homogenized strand of the molding compositions is drawn off, cooled in a water bath, and then pelletized.

In another embodiment, in an extruder, the mixed salts of diorganylphosphinic acids and carboxylic acids, and/or the flame retardants, and/or the additives are metered via a side intake into the polymer stream, and homogenized.

A process for the preparation of a flame-retardant polymer molding composition comprises polymerizing 1000 parts by weight of dimethyl terephthalate and 720 parts by weight of ethylene glycol, and from 35 to 700 parts by weight of diethylphosphinic acid of the invention. The polymerization reaction can optionally take place in the presence of zinc acetate. The flame-retardant polymer molding composition can optionally be spun to give fibers.

It is preferable that the processing temperatures during the processes for the preparation of the polymer molding compositions of the invention are from 170 to 200° C. for polystyrene, from 200 to 300° C. for polypropylene, from 250 to 290° C. for polyethylene terephthalate (PET), from 230 to 270° C. for polybutylene terephthalate (PBT), from 260 to 290° C. for nylon-6 (PA 6), from 260 to 290° C. for nylon-6,6 (PA 6.6), and from 280 to 320° C. for polycarbonate. The homogenized polymer strand is drawn off, cooled in a water bath, and then pelletized, and dried until its residual moisture content is from 0.05 to 5%, preferably from 0.1 to 1% by weight.

It is preferable that effective screw lengths (L) of the extruder, as a function of the screw diameter (D), in this type of process are from 4 to 200D, preferably from 10 to 50D.

Single-screw extruders, for example from Berstorff GmbH, Hanover, and/or from Leistritz, Nuremberg, are suitable compounding assemblies.

Multizone-screw extruders having three-zone screws and/or short compression screws are suitable compounding assemblies.

Co-kneaders, e.g. from Coperion Buss Compounding Systems, Pratteln, Switzerland, e.g. MDK/E46-11D, and/or laboratory kneaders (MDK 46 from Buss, Switzerland, with L=11D), are suitable compound assemblies.

Twin-screw extruders, e.g., from Coperion Werner & Pfleiderer GmbH & Co. KG, Stuttgart (ZSK 25, ZSK30, ZSK 40, ZSK 58, ZSK MEGAcompounder 40, 50, 58, 70, 92, 119, 177, 250, 320, 350, 380), and/or from Berstorff GmbH, Hanover, and/or from Leistritz Extrusionstechnik GmbH, Nuremberg, are suitable compounding assemblies.

Ring extruders, e.g. from 3+Extruder GmbH, Laufen, with a ring of from three to twelve small screws rotating around a static core, and/or planetary-gear extruders, e.g. from Entex, Bochum, and/or vented extruders, and/or cascade extruders, and/or Maillefer screws, are suitable compounding assemblies.

Compounders with a counter-rotating twin screw are suitable compounding assemblies, examples being the Compex 37 or 70 from Krauss-Maffei Berstorff. For single-screw extruders, effective screw lengths of the invention are from 20 to 40 D.

For multizone-screw extruders, examples of effective screw lengths (L) are 25 D with feed zone (L=10 D), transition zone (L=6 D), and metering zone (L=9 D).

Effective screw lengths for twin-screw extruders are from 8 to 48 D.

The flame-retardant polymer molding composition is preferably in pellet form (compounded material). The pellet preferably has the shape of a cylinder with circular, elliptical, or irregular base, or of a sphere, cushion, cube, parallelepiped, and/or prism.

The length-to-diameter ratio of the pellet is from 1:50 to 50:1, preferably from 1:5 to 5:1.

It is preferable that the diameter of the pellet is from 0.5 to 15 mm, particularly from 2 to 3 mm, and that its length is from 0.5 to 15 mm, particularly from 2 to 5 mm.

The pellets obtained are dried by way of example for 10 h at 90° C. in a convection oven.

It is preferable that the process for the production of flame-retardant polymer moldings processes a flame-retardant polymer molding composition by injection molding and compression molding, foam injection molding, internal-gas-pressure injection molding, blow molding, film casting, calendering, laminating, coating, etc., to give the flame-retardant polymer molding.

The processing temperatures in the abovementioned process are from 200 to 250° C. for polystyrene, from 200 to 300° C. for polypropylene, from 250 to 290° C. for polyethylene terephthalate (PET), from 230 to 280° C. for polybutylene terephthalate (PBT), from 260 to 290° C. for nylon-6 (PA 6), from 260 to 295° C. for nylon-6,6 (PA 6.6), and from 280 to 320° C. for polycarbonate.

The flame-retardant polymer molding compositions of the invention are suitable for the production of fibers, of foils, and of moldings, and in particular for applications in the electrical and electronic sector.

The invention gives preference to the use of the flame-retardant polymer moldings of the invention as lamp parts, such as lamp sockets and lamp holders, plugs and multipoint connectors, coil formers, casings for capacitors or connectors, and circuit-breakers, relay housings, and reflectors.

UL 94 (Underwriters Laboratories) fire classification was determined on test specimens composed of each mixture, using test specimens of thickness 1.6 mm.

The UL 94 fire classifications are as follows:

V-0: afterflame time never longer than 10 sec, total of afterflame times for 10 flame applications not more than 50 sec, no flaming drops, no complete consumption of the specimen, afterglow time for specimens never longer than 30 sec after end of flame application V-1: afterflame time never longer than 30 sec after end of flame application, total of afterflame time for 10 flame applications not more than 250 sec, afterglow time for specimens never longer than 60 sec after end of flame application, other criteria as for V-0

V-2: cotton indicator ignited by flaming drops, other criteria as for V-1 not classifiable (ncl): does not comply with fire classification V-2.

EXAMPLE 1

A mixture of 5 g of terephthalic acid and 1.2 g of aluminum trisdiethylphosphinate is used in a porcelain boat in an electrically heated tubular furnace. Under a stream of dry nitrogen (30 l/h), the mixture is heated to 350° C. and this temperature is maintained for 0.5 h. The yield obtained of the product is 97%. The X-ray powder diffractogram of the product shows the typical reflections cited in example 4 for aluminum mono (diethylphosphinate)terephthalate.

Under the conditions of the invention, a flame-retardant polymer molding composition composed of 30% by weight of glass fibers (Vetrotex® EC 10 983, Saint-Gobain), 45% by weight of nylon-6,6 (Ultramid® A3, BASF), and 25% by weight of mixed salt of the invention is compounded at 275° C. in a twin-screw extruder. The homogenized polymer strand is drawn off, cooled in a water bath, and then pelletized. After drying, the molding compositions are processed in an injection-molding machine at melt temperatures of 295° C. to give polymer moldings (test specimens whose dimensions correspond to the UL 94 standard). The test specimens achieved V-1 classification at 1.6 mm thickness in the UL 94 fire test.

EXAMPLE 2

A mixture of 5 g of terephthalic acid and 3.9 g of aluminum trisdiethylphosphinate is reacted for 0.5 h at 300° C., as in example 1. The X-ray powder diffractogram of the product shows the typical reflections cited in example 4 for aluminum mono(diethylphosphinate)terephthalate, but the product also still comprises about 10% of aluminum trisdiethylphosphinate, the yield being 90%.

EXAMPLE 3

A mixture of 5 g of terephthalic acid and 3.9 g of aluminum trisdiethylphosphinate is reacted for 3 min at 350° C., as in example 1. The X-ray powder diffractogram of the product shows the typical reflections cited in example 4 for aluminum mono(diethylphosphinate)terephthalate, but the product also still comprises about 25% of aluminum trisdiethylphosphinate, the yield being 75%.

The product is therefore a flame retardant of the invention, which comprises not only a mixed salt of diorganylphosphinic acid and carboxylic acid but also aluminum trisdiethylphosphinate. Although this flame retardant mixture comprises a certain content of aluminum trisdiethylphosphinate, it nevertheless has very good properties.

Under the conditions of the invention, a flame-retardant polymer molding composition composed of 30% by weight of glass fibers (Vetrotex® EC 10 983, Saint-Gobain), 50% by weight of nylon-6,6 (Ultramid® A3, BASF), and 20% by weight of flame retardant of the invention (constitution: 75% by weight of mixed salt, 25% of aluminum trisdiethylphosphinate) is compounded at 275° C. in a twin-screw extruder. The homogenized polymer strand is drawn off, cooled in a water bath, and then pelletized. After drying, the molding compositions are processed in an injection-molding machine at melt temperatures of 295° C. to give polymer moldings (test specimens whose dimensions correspond to the UL 94 standard). The test specimens achieved V-0 classification at 1.6 mm thickness in the UL 94 fire test.

EXAMPLE 4

A mixture of 5 g of terephthalic acid and 3.9 g of aluminum trisdiethylphosphinate is reacted for 0.5 h at 350° C., as in example 1. The yield is 97%. Aluminum content is 8.1% by weight (th. 8.6), and P content is 9.4% by weight (th. 9.9%), in agreement with the stoichiometry of "aluminum mono (diethylphosphinate)terephthalate". Decomposition in differential thermal analysis (2% weight loss, atmosphere: air) takes place at 425° C. In contrast to this, aluminum trisdiethylphosphinate decomposes at a temperature as low as 355° C., and aluminum terephthalate at a temperature as low as 298° C., under the same conditions. The reflections in the X-ray powder diffractogram (XRD) are characteristic: d values (intensity) 9.05 Ang (st), 12.15 (st), 17.46 (m), 18.52 (m), 24.15 (m), 24.95 (m).

Under the conditions of the invention, a flame-retardant polymer molding composition composed of 30% by weight of glass fibers (Vetrotex® EC 10 952, Saint-Gobain), 50% by weight of polybutylene terephthalate (Ultradur® B 4500, BASF), and 20% by weight of flame retardant mixture of the invention is compounded at 256° C. in a twin-screw extruder. The flame retardant mixture of the invention is composed of 75% by weight of mixed salts of example 4 and 25% by weight of Exolit® OP 1240 (aluminum trisdiethylphosphinate), Clariant. The homogenized polymer strand is drawn off, cooled in a water bath, and then pelletized. After drying, the molding compositions are processed in an injection-molding machine at melt temperatures of 280° C. to give polymer moldings (test specimens whose dimensions correspond to the UL 94 standard). The test specimens achieved V-0 classification at 1.6 mm thickness in the UL 94 fire test.

When 25% by weight of mixed salt of example 4 and 75% by weight of Exolit® OP 1240 (aluminum trisdiethylphosphinate) are used under identical conditions, the test specimens achieve V-1 classification at 1.6 mm thickness in the UL 94 fire test.

EXAMPLE 5

A mixture of 5 g of terephthalic acid and 3.9 g of aluminum trisdiethylphosphinate is reacted for 5 h at 350° C., as in example 1. The X-ray powder diffractogram of the product shows the typical reflections cited in example 4 for aluminum mono(diethylphosphinate)terephthalate. The yield is 95%.

EXAMPLE 6

A mixture of 5 g of terephthalic acid and 3.9 g of aluminum trisdiethylphosphinate is reacted for 0.5 h at 400° C., as in example 1. The X-ray powder diffractogram of the product shows the typical reflections cited in example 4 for aluminum mono(diethylphosphinate)terephthalate. The yield is 95%.

EXAMPLE 7

A mixture of 1.7 g of terephthalic acid and 3.9 g of aluminum trisdiethylphosphinate is reacted for 0.5 h at 350° C., as in example 1. The X-ray powder diffractogram of the product shows the typical reflections cited in example 4 for aluminum mono(diethylphosphinate)terephthalate. The yield is 90%.

EXAMPLE 8

A mixture of 0.2 g of terephthalic acid and 3.9 g of aluminum trisdiethylphosphinate is reacted for 0.5 h at 350° C., as in example 1. The X-ray powder diffractogram of the product shows the typical reflections cited in example 4 for aluminum mono(diethylphosphinate)terephthalate, but the product also still comprises about 93% of aluminum trisdiethylphosphinate, the yield being 7%.

EXAMPLE 9

A mixture of 5 g of isophthalic acid and 3.9 g of aluminum trisdiethylphosphinate is reacted for 0.5 h at 350° C., as in example 1. The yield is 98%. The reflections in the X-ray powder diffractogram (XRD) are characteristic: d values (intensity) 10.79 Ang (st), 8,14 (st), 7,19 (st). Aluminum content is 8.2% by weight (th. 8.6), and P content is 9.5% by weight (th. 9.9%), in agreement with the stoichiometry of "aluminum mono(diethylphosphinate)isophthalate".

EXAMPLE 10

A mixture of 3.8 g of nitrilotriacetic acid and 3.9 g of aluminum trisdiethylphosphinate is reacted for 0.5 h at 250° C., as in example 1. The yield is 75%. The X-ray powder diffractogram of the product shows a typical reflection at a d value (intensity) of 9.1 Ang (st), but the product also comprises about 25% of aluminum trisdiethylphosphinate.

EXAMPLE 11

A mixture of 5.7 g of epsilon-caprolactam and 3.9 g of aluminum trisdiethylphosphinate is reacted for 5 h at 350° C. The yield is 96%. Aluminum content is 7.2% by weight (th. 9.1), and P content is 8.9% by weight (th. 8.3%), in agreement with the stoichiometry of "aluminum mono(ethylmethylphosphinate)di(epsilon-aminocapronate)".

EXAMPLE 12

A mixture of 3.2 g of terephthalonitrile and 3.9 g of aluminum trisdiethylphosphinate is reacted for 1 h at 230° C., as in example 1, but under a stream of dry nitrogen (30 l/h) comprising 17 g/m$^3$ of water. The X-ray powder diffractogram of the product shows the typical reflections cited in example 4 for aluminum mono(diethylphosphinate)terephthalate, but the product still comprises about 35% of aluminum trisdiethylphosphinate, the yield being 65%.

EXAMPLE 13

A mixture of 6.6 g of terephthalic acid and 3.1 g of zinc bisdiethylphosphinate is reacted for 2 h at 390° C., as in example 1. The yield is 85%. The X-ray powder diffractogram of the product exhibits typical reflection at the following d values (intensity): 9.21 Ang (st), 5.49 (st), but the product still comprises about 15% of zinc bisdiethylphosphinate.

EXAMPLE 14

A mixture of 5 g of terephthalic acid and 2.2 g of aluminum trisphosphinate is reacted for 10 h at 200° C., as in example 1. The yield is 95%. Aluminum content is 9.9% by weight (th. 10.5), and P content is 10.5% by weight (th. 12.1%), in agreement with the stoichiometry of "aluminum mono(phosphinate)terephthalate".

EXAMPLE 15

An intimate mixture of 4.3 g of ethylmethylphosphinic acid and 2.7 g of dialuminum triterephthalate is used in a porcelain boat in an electrically heated tubular furnace. Under a stream of dry nitrogen (30 l/h), the mixture is heated to 300° C. and this temperature is maintained for 0.5 h. The yield obtained of the product is 95%. Aluminum content is 8.8% by weight (th. 9.1), and P content is 10.1% by weight (th. 10.4%), in agreement with the stoichiometry of "aluminum mono(ethylmethylphosphinate)terephthalate".

EXAMPLE 16

83.1 g of terephthalic acid, 63 g of bishydroxymethylphosphinic acid and 39 g of aluminum trihydroxide are heated for 24 h to 270° C. in an autoclave from Berghoff (electrically heated, with PTFE inner capsule). The product yield obtained is 95%. Aluminum content is 8.7% by weight (th. 8.5), and P content is 9.3% by weight (th. 9.8%), in agreement with the stoichiometry of "aluminum mono(bishydroxymethylphosphinate)terephthalate".

TABLE

| | Chemicals used | | | | | | | | | | | | |
|---|---|---|---|---|---|---|---|---|---|---|---|---|---|
| | Acid | | Phosphinic acid source | | Cation source | | Quotient of acid/cation source [mol/mol] | Quotient of phosphinic acid/cation source [mol/mol] | Process | T [° C.] | t [h] | Yield [%] | Cation content [%] | P content [%] |
| Ex. | Type | Amount [g] | Type | Amount [g] | Type | Amount [g] | | | | | | | | |
| 1 | TPA | 5.0 | — | 0 | ATP1 | 1.2 | 10 | 0 | 2 | 350 | 0.5 | 97 | — | — |
| 2 | TPA | 5.0 | — | 0 | ATP1 | 3.9 | 3 | 0 | 2 | 300 | 0.5 | 90 | — | — |
| 3 | TPA | 5.0 | — | 0 | ATP1 | 3.9 | 3 | 0 | 2 | 350 | 0.05 | 75 | — | — |
| 4 | TPA | 5.0 | — | 0 | ATP1 | 3.9 | 3 | 0 | 2 | 350 | 0.5 | 97 | 8.1 | 9.5 |
| 5 | TPA | 5.0 | — | 0 | ATP1 | 3.9 | 3 | 0 | 2 | 350 | 5 | 95 | — | — |
| 6 | TPA | 5.0 | — | 0 | ATP1 | 3.9 | 3 | 0 | 2 | 400 | 0.5 | 95 | — | — |
| 7 | TPA | 1.7 | — | 0 | ATP1 | 3.9 | 1 | 0 | 2 | 350 | 0.5 | 90 | — | — |
| 8 | TPA | 0.2 | — | 0 | ATP1 | 3.9 | 0.1 | 0 | 2 | 350 | 0.5 | 7 | — | — |
| 9 | IPA | 5.0 | — | 0 | ATP1 | 3.9 | 3 | 0 | 2 | 350 | 0.5 | 98 | 8.2 | 9.5 |
| 10 | NTA | 3.8 | — | 0 | ATP1 | 3.9 | 2 | 0 | 2 | 250 | 0.5 | 75 | — | — |
| 11 | ECL | 5.7 | — | 0 | ATP1 | 3.9 | 5 | 0 | 2 | 350 | 5 | 96 | 7.0 | 8.9 |
| 12 | TPD | 3.2 | — | 0 | ATP1 | 3.9 | 2.5 | 0 | 2 | 230 | 1 | 65 | — | — |
| 13 | TPA | 6.6 | — | 0 | ZDP | 3.1 | 4 | 0 | 2 | 390 | 2 | 85 | — | — |
| 14 | TPA | 5.0 | — | 0 | ATP2 | 2.2 | 3 | 0 | 2 | 200 | 10 | 95 | 9.9 | 10.5 |

TABLE-continued

| | Acid | | Phosphinic acid source | | Cation source | | Quotient of acid/cation source [mol/mol] | Quotient of phosphinic acid/cation source [mol/mol] | Process | T [°C.] | t [h] | Yield [%] | Cation content [%] | P content [%] |
|---|---|---|---|---|---|---|---|---|---|---|---|---|---|---|
| Ex. | Type | Amount [g] | Type | Amount [g] | Type | Amount [g] | | | | | | | | |
| 15 | — | 0 | EMP | 4.3 | ATP3 | 2.7 | 0 | 4 | 1 | 300 | 0.5 | 95 | 8.8 | 10.1 |
| 16 | TPA | 83.1 | BHP | 63.0 | ATH | 39 | 1 | 1 | 3 | 270 | 24 | 95 | 8.7 | 9.3 |

TPA Terephthalic acid
IPA Isophthalic acid
NTA Nitrilotriacetic acid
ATP1 Aluminum trisdiethylphosphinate
ZDP Zinc bisdiethylphosphinate
ATP2 Aluminum trisphosphinate
EMP Ethylmethylphosphinic acid
ATP3 Dialuminum triterephthalate
ATH Aluminum trihydroxide
BHP Bishydroxymethylphosphinic acid
ECL Epsilon-caprolactam
TPD Terephthalodinitrile In example 3 and 4, the flame retardants and flame retardant mixtures of the invention permit higher injection-molding temperatures than the prior art.

The invention claimed is:

1. A mixed salt of diorganylphosphinic acids and carboxylic acids of the formula

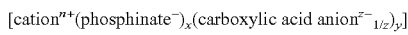

wherein
n=from 1 to 4
x=from 0.01 to n−0.01
y=n−x
z=from 1 to 4,
wherein
the cation is an element of the second main and/or transition group, an element of the third main and/or transition group, an element of the fourth main and/or transition group, an element of the fifth main and/or transition group, an element of the sixth transition group, an element of the seventh transition group, and/or an element of the eighth transition group or a combination thereof, the phosphinate is an anion of diorganylphosphinic acids of the formula

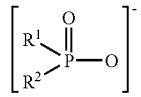

wherein
R$^1$ and R$^2$ are identical or different and, independently of one another, methyl, ethyl, n-propyl, isopropyl, n-butyl, sec-butyl, tert-butyl, n-pentyl, phenyl, hydroxymethyl, hydroxyethyl or hydroxypropyl,
and
carboxylic acid anion is a $C_1$-$C_{18}$ carboxylic acid anion.

2. The mixed salt as claimed in claim 1, wherein the cation is at least one selected from the group consisting of Mg, Ca, Al, Sb, Sn, Ge, Ti, Fe, Zr, Zn, Ce, Bi, Sr and Mn.

3. The mixed salt as claimed in claim 1, wherein the carboxylic acids are polybasic or aromatic $C_8$-$C_{18}$ carboxylic acids or $C_8$-$C_{18}$ omega-aminocarboxylic acids.

4. A flame retardant or a mixture of flame retardants comprising at least one mixed salt of diorganylphosphinic acids and carboxylic acids as claimed in claim 1.

5. A flame retardant, comprising
a) from 0.1% to 99.9% by weight of at least one mixed salt of diorganylphosphinic acids and carboxylic acids, as claimed in claim 1; and
b) from 0.1% to 99.9% by weight of at least one cation source.

6. A flame retardant booster, a flame retardant for clearcoat lacquers or intumescent coatings, a flame retardant for wood or other cellulose-containing products, a reactive or non-reactive flame retardant for polymers, or a flame retardancy agent for polyester and to unblended or blended cellulose textiles, via impregnation, comprising at least one mixed salt of diorganylphosphinic acids as claimed in claim 1.

7. A composition comprising at least one mixed salt of diorganylphosphinic acids and carboxylic acids as claimed in claim 1, wherein the composition is selected from the group consisting of binders for foundry materials or molding sands; crosslinking agents or accelerators in the hardening of epoxy resins, polyurethanes, or unsaturated polyester resins; polymer stabilizers; light stabilizers, free-radical scavengers, or heat stabilizers for cotton fabrics, polymer fibers, plastics; crop protection agents; plant growth regulators; herbicides; presticides; fungicides;
therapeutic agents or additives in therapeutic agents for humans and animals;
enzyme modulators; tissue growth stimulators;
sequestering agents; deposit control agents in industrial water supply systems, in petroleum production, or in metal-treatment agents;
petroleum additives, antioxidants, agents for increasing octane number; corrosion-prevention agents;
laundry-detergent or cleaning-product applications; decolorizers;
polyelectrolytes for capacitors, batteries, and accumulators; free-radical scavengers in photosensitive layers;
aldehyde scavengers; and
formaldehyde scavengers in adhesive compositions or in moldings for construction applications, in the automobile industry, in shipbuilding, in the aerospace industry, and for electrical engineering.

8. A flame-retardant polymer molding composition, comprising
from 0.1 to 39% by weight of at least one mixed salt of diorganylphosphinic acids and carboxylic acids as claimed in claim 1,
from 0.5 to 98.9% by weight of polymer or of a mixture of polymers,
from 0.5 to 50% by weight of at least one additive, and
from 0 to 50% by weight of at least filler or reinforcing material,
where the entirety of the components is 100% by weight.

9. A flame-retardant polymer molding composition, comprising
from 0.5 to 45% by weight of a flame retardant or a flame retardant mixture comprising at least one mixed salt of diorganylphosphinic acids and carboxylic acids as claimed in claim 1,
from 0.5 to 98.5% by weight of polymer or of a mixture of polymers,
from 0.5 to 50% by weight of at least one additive, and
from 0 to 50% by weight of at least one filler or reinforcing material,
where the entirety of the components is 100% by weight.

10. A flame-retardant polymer molding, a flame-retardant film, a flame-retardant filament, or a flame-retardant fiber, comprising from 1 to 50% by weight of at least one mixed salt of diorganylphosphinic acids and carboxylic acids as claimed in claim 1, a flame retardant or a flame retardant mixture comprising at least one mixed salt of diorganylphosphinic acids and carboxylic acids as claimed in claim 1,
from 1 to 99% by weight of polymer or a mixture of polymers,
from 0 to 60% by weight of at least one additive, and
from 0 to 60% by weight of filler,
where the entirety of the components is 100% by weight.

11. A mixed salt of diorganylphosphinic acids and carboxylic acids of the formula

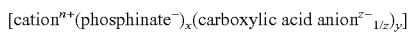

wherein
n=from 1 to 4
x=from 0.01 to n−0.01
y=n−x
z=from 1 to 4,
wherein
the cation is an element of the second main and/or transition group, an element of the third main and/or transition group, an element of the fourth main and/or transition group, an element of the fifth main and/or transition group, an element of the sixth transition group, an element of the seventh transition group, and/or an element of the eighth transition group or a combination thereof,
the phosphinate is an anion of diorganylphosphinic acids of the formula

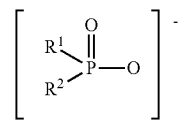

wherein
$R^1$ and $R^2$ are identical or different and, independently of one another, are H, $C_1$-$C_6$-alkyl, linear or branched, aryl, or hydroxyalkyl, and
wherein the carboxylic acids are terephthalic acid, phthalic acid, isophthalic acid, or ethylene glycol-terephthalic acid oligomer.

12. A mixed salt of diorganylphosphinic acids and carboxylic acids
wherein the mixed salt is aluminum isophthalate diethylphosphinate, aluminum terephthalate diethylphosphinate, or dizinc monoterephthalate mono(diethylphosphinate).

* * * * *